ABSTRACTAn electro-dynamic transducer head (107) coming into contact with a workpiece (14) comprises a protective cap (28, 38), which is at least partially surrounded by a sliding protection element (22). The sliding protective element has a basic member (24) with sections (26), which are introduced into recesses (28) by deposit welding.
15 Claims, 3 Drawing Figures
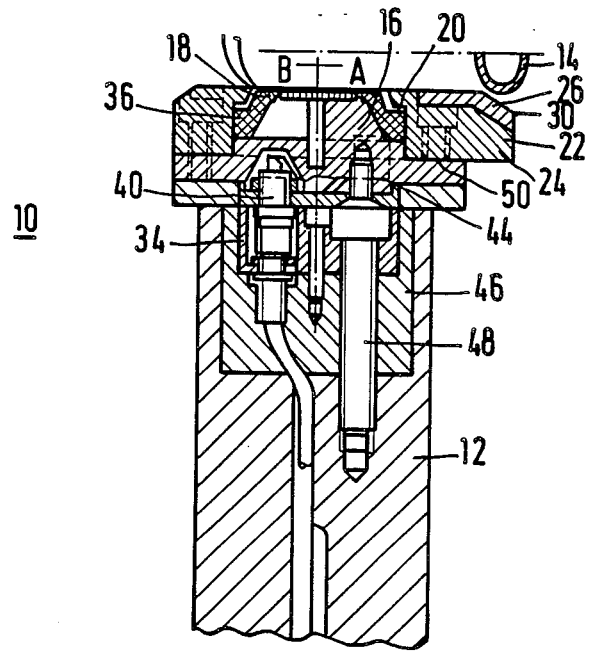

ELECTRO-DYNAMIC TRANSDUCER

BACKGROUND OF THE INVENTION

1. Field of the Invention

The invention relates to an electro-dynamic transducer for non-destructive testing of workpieces by means of ultra-sonics. It consists of a magnet with a magnet yoke with external pole shoe surrounding a conically-shaped inner pole shoe. This inner pole shoe is tapered preferably towards the workpiece, and equipped in the region of its free face opposite to the workpiece with exciter and receiver coils, which in turn are provided with a cover at least on the side facing the workpiece.

2. Description of Prior Art

A corresponding electro-dynamic transducer can be seen from GB-A-20 06 433. The magnet, which—as usual—takes the form of an electro-magnet, comprises two coaxially arranged poles the geometries of the sides facing the workpiece to be tested corresponding to the geometry of the workpiece. Arranged on the front face of the inner pole shoe, which also consists of two mutually arranged coaxially arranged sections, is an exciter coil and a receiver coil. The workpiece side of this coil is covered by a layer of ceramic material, whereas the magnet pole side is covered by an insulating layer. If the pole shoes are appropriately designed then, amongst other things, feed-back from the workpiece under test and associated generation of eddy currents in the pole shoes can have an adverse influence on the resolution of the measurement signal. Neither is it possible to lower an appropriate electro-dynamic transducer head in the area of the exciter and receiver coil directly onto the workpiece in order to carry out measurements with a rotating electro-magnet and/or rotating workpiece. This is because the surface of the exciter and receiver coil would be immediately destroyed by the abrasive effect of the workpiece. The cover made of ceramic material is not highly impact-resistant however.

Described in the DE-A-31 23 935 is an electro-dynamic transducer, which also contains an inner pole shoe surrounded by an external pole shoe, whereby the inner pole shoe has on its face an exciter and receiver coil in addition to radially orientated slots into which transformer stampings can be placed, if required. The aim of this feature is to eliminate feed-back from the tested workpiece to the pole shoes, thus enabling high resolution of the measurement values. An appropriate electro-dynamic transducer head cannot, however, be lowered onto the tested workpiece—particularly a tube—and also moved, since this would result in immediate destruction of the measurement system.

In the European Patent Registration 00 45 412 and the British Letters Patent 14 25 201 electro-dynamic transducers are described in which the exciter and receiver coils are arranged on the inner pole shoe of a magnet with heating insulation. During measurement a clearance is left between the face of the transducer and the workpiece to be tested. For this purpose an air cushion is generated between the workpiece and the transducer in accordance with GB-PS 14 25 520. Described in DE-OS 28 45 579 is a transducer in which the surfaces of an inner pole shoe and the surrounding outer pole shoes are concave, and matched to the exterior shape of the workpiece being tested. The curved surfaces of the pole shoes are also spaced from the surface of the workpiece.

SUMMARY OF THE INVENTION

The aim of this invention is to design an electro-dynamic transducer of the previously described type, such that said electro-dynamic transducer can be lowered without risk onto a workpiece, in particular a pipe, so that these move relative to each other without resulting in destruction of the exciter and receiver coil.

According to the invention the task is achieved in that the cover includes a protective cap, which is spaced from the exciter and receiver coil, and covers it. The protective cap in turn is partially covered by a sliding protection element, which has a basic member with sections which come into contact with the workpiece. These sections are formed by metal particles fused into a matrix, and applied to recesses in the basic member by deposit welding. On the side of the basic member facing the workpiece these deposit welded sections project at least in part relative the basic member, which can also be described as a carrier. The matrix itself preferably consists of carbon steel and the metal particles of hard alloy, with hardnesses lying between 1.500 VHN (=Vickers Hardness Number) to 2.500 VHN, preferably in the range around 2.000 VHN. Finally the basic member should consist of an austenitic steel. The use of austenitic steel for the basic member has the advantage that fractures cannot propagate in this material, even if a crack occurs in the deposit welding because of inept lowering of the transducer onto a workpiece.

Due to the features described above—which in combination and individually are fundemental to the invention—protection which is impact-resistant, hard-wearing and temperature-resistant is provided for the first time for an electro-dynamic transducer head. In addition, the basic member can also be ground to shape, i.e., have chamfered end-sections on the surfaces running parallel to the workpiece to be scanned, in order to absorb forces in the event of abrupt lowering of the transducer onto the workpiece, thereby eliminating the risk of destroying the cover.

The sections produced by deposit welding—which of course can be flush ground into the recesses after being applied to the basic member—can very generally be described as armoring. This armoring ensures that the elements vital to measurement, i.e., exciter and receiver coils, will not be destroyed in spite of sliding along the surface of the workpiece to be tested. The invented cover thus permits the electro-dynamic transducer to rotate at 1000 revolutions per minute around and on the surface of a tubular workpiece without fear of damage, even when the surface is rendered particularly rough by burrs and similar irregularities and is comparable to an emery cloth.

Further uniquely original features of this invention worth particularly emphasizing are the designs of the protective caps. Hereby the protective cap can preferably be made out of metal with a nitrated surface and have radial slots in order to prevent development of eddy currents. The protective cap itself—which takes the shape of a truncated cone and which has a rim running around the bottom preferably parallel to the face—is in contact on the pole-shoe side with a cap carrier preferably made of a mixture of laminated fabric and epoxy-resin; the cap carrier is in contact with the side of the tapered head section of the inner pole shoe. The protective cap is accordingly fixed between sections of the basic member of the sliding protective element and the cap carrier. So that the protective cap, which is spaced from the exciter and receiver coil, does not have a negative effect on the measurement results, the thickness of its material is kept small.

For preference the gage for a diameter from approximately 20 to 30 mm lies in the range between 0.3 and 0.5 mm; the 0.4 mm gage must be specially mentioned. The radially running slots let into the protective cap should have a width equal to less than the thickness of the protective cap material. For instance, the width can lie between 0.2 and 0.4 mm whereby an average value of 0.3 mm should be particularly suitable. Moreover, the slots should preferably terminate at a short distance from the centre point of the protective cap in order not to have an adverse effect on its strength.

It is particularly advantageous if the inside surface of the protective cap, i.e., the surface facing the coils, is clad in a resin bonded fabric layer also consisting of an epoxy-resin mixture. This ensures that particles of metal abraided from the workpiece being tested cannot penetrate through the slots in the region of the coils. In order to enhance sealing of the slots, it is preferable to bond the resin bonded fabric layer to the internal surface.

In accordance with a further unique design feature of the invention, the protective cap covering the coils is formed out of layers of synthetic stone, such as sapphire. The sapphire layer can hereby be provided with a resin bonded fabric coating on the coil side in order to increase the strength of the layer of synthetic stone. The gage of this layer of synthetic stone as well as that of the resin bonded fabric should lie in the range 0.2 to 0.3 mm. The protective cap takes the form of a cylindrical disc made of a layer of synthetic stone, and can be inserted into a cap carrier of the type previously mentioned. The protective cap offers the advantage that no adverse effect results in the signals to be evaluated, in spite of screening the coil in respect of the workpiece.

In accordance with a further form of design of the invention, the sliding protection element with the protective cap, the cap carrier, a section of the inner pole shoe facing the workpiece and the exciter and receiver coil mounted on it, together form an exchangeable transducer head, which can be linked with a lower part of the inner pole by means of a plug-and-socket connector. Finally, the sliding protection element itself can be removed from the transducer head, and exchanged, insofar as an inspection is required. This feature too results in so-called user friendliness.

BRIEF DESCRIPTION OF THE DRAWINGS

The invention is explained in greater detail on the basis of an embodiment taken from the drawing.

The following show.

DETAILED DESCRIPTION OF THE PRESENTLY PREFERRED EXEMPLARY EMBODIMENTS

Figure 1:
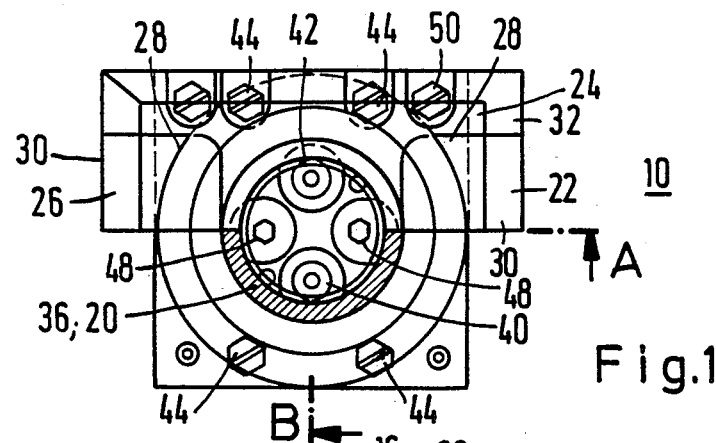
FIG. 1 Plan elevation of an electro-dynamic transducer head.
Figure 2:
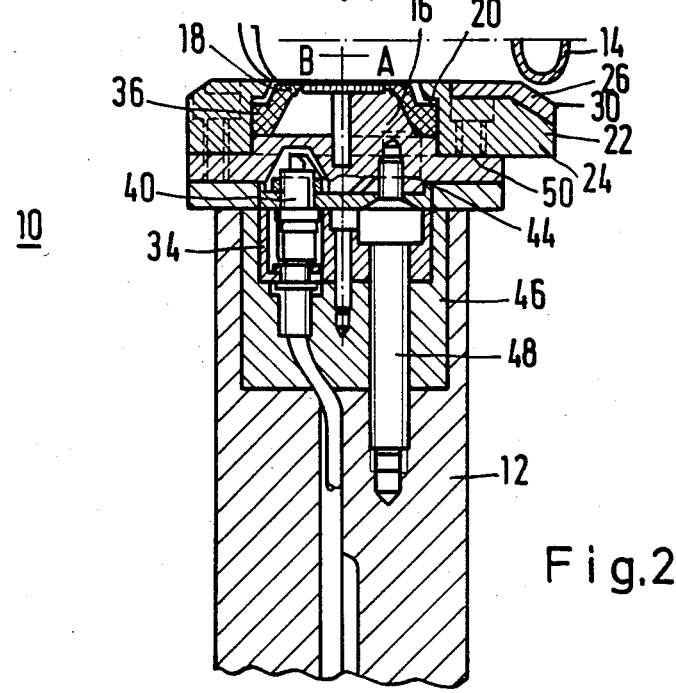
FIG. 2 Cross-sectional illustration of the electro-dynamic transducer head as in FIG. 1 along the line A-B, and FIG. 3 Detail drawing of a protective cap for the electro-dynamic transducer head according to FIGS. 1 and 2.
Figure 3:
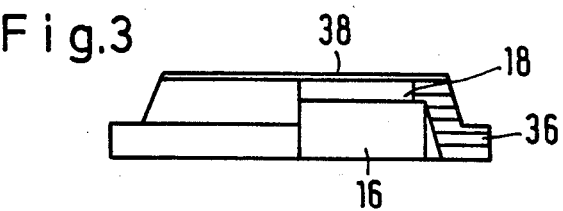

The electro-dynamic transducer head 10 shown in FIGS. 1 and 2 is part of a transducer, which encompasses an electro-magnet having a magnet yoke with an outer pole shoe (not illustrated) and an inner pole shoe 12 which it surrpounds. The inner pole shoe 12, which is directed at a tubular workpiece 14, has a narrowed section 16 at the workpiece 14 end. This section 16 has radially oriented slots (not necessarily illustrated) into which insulated transformer stampings (also not illustrated) can be introduced. Appropriate design of the pole shoe head 16 ensures that eddy currents cannot form in it whereby the measurements could otherwise be falsified. On the face of the pole shoe head 16 is an exciter and receiver coil (not described in further detail) necessary for the electro-dynamic excitation. (As is familiar, the electro-dynamic generation of ultra-sonic energy in electrically conductive media is based on the interaction of eddy currents with static magnetic fields, whereby particle movement in the workpiece, i.e., the ultra-sonic waves, is generated. The necessary magnetic field should preferably be generated by an electro-magnet through a desired pole shoe configuration. The high-frequency currents flowing in the wires of the excitation coil generate eddy currents in the workpiece, the penetration depth of which depends on the frequency used).

In order to be able to set down the test head 10 onto the tube 14 in the area of the inner pole shoe 16 without relative motion between these two leading to damage of the exciter and receiver coil, the face surface 18 of the pole shoe 16, and thus of the exciter and receiver coil, is fitted with protective cap 20 extending over the complete face surface 18. Because the protective cap 20 must be of thin gage material in the region of the face surface 18, so as to exclude adverse effects on the measurement signals, the protective cap 20 itself is at least partially enclosed in sliding protection element 22. The sliding protection element 22 in this case comprises a basic member 24, or carrier and the sections 26 which, in turn, come into direct contact with workpiece 14, and consequently protrude beyond the remaining surface of the basic member 24 facing the workpiece 14. According to the invention, the sections 26 are formed in recesses 28 in the basic member by deposit welding of metal particles fused into a matrix. The sections 26 are thus represented by the deposit welding, which in turn form an armoring. In this case the metal particles are of hard alloy, whereas the matrix is made of carbon steel. The basic member 24, or carrier for the abrasion-resistant sections 26 is made of austenitic steel ensuring that even if fractures do occur they will not propagate into the carrier 24.

As illustrated in FIGS. 1 and 2, the sections 26 have a cuboid shape. Other geometries are, of course, possible. Hereby the sections 26 are ground to shape in their outer regions 30, i.e., they are chamfered away from the surface of the workpiece 14. The advantage of this is that, in the event of inexpert lowering of the transducer head 10 onto the workpiece 14, energy will be absorbed; this would to a great extent prevent destruction of the transducer head 10. The adjacent sections 32 of carrier 24 in area 30 are also ground to shape, of course.

The protective cap 20 is accepted by a cap carrier 36, which in turn is in contact with the sides of the conicalshaped inner pole shoe 16. The cap carrier 36 consists preferably of a resin bonded fabric (HgwEpox) in the form of an epoxy-resin mixture. The geometry of the external surface of the cap carrier 36 is hereby matched to that of the protective cap 20 clear of the face area of pole shoe 16.

The protective cap 20 itself preferably takes the form of a truncated conical section, the lower peripheral edge of which is chamfered to the outside. Furthermore, the protective cap 20 consists preferably of metal with nitrated surface, and features radially arranged slots to prevent the formation of eddy currents. Moreover, the inside surface of the protective cap 20 is covered in a resin bonded fabric layer so as to ensure that particles abraided off the body of the workpiece cannot penetrate through into the slots. The resin bonded fabric layer should preferably be stuck to the cap carrier.

Alternatively the protective cap 20 can be replaced by a flush layer of synthetic stone 38, for example sapphire, set into the cap carrier 36. This almost completely excludes any effects on the measurement signals through the protective cap. The layer 38, comprising of synthetic stone, can thereby be covered on the coil side by a layer of resin bonded fabric so as to increase its stability. Corresponding design of the protective cap is specially worth mentioning.

As FIG. 2 shows, the transducer head 10 is linked to the inner pole shoe in the same way as a plug-and-socket connection. Thereby the transducer head 10 encompasses the sliding protection element 22, the protective cap 20 with protective cap carrier 36, the upper section of pole shoe 12 with the conical end 16, together with the exciter and receiver coil, as well as electrical connectors 40, 42 via which the link is established between the coils and the electrode (not described in any more detail). This unit containing the elements described above can now be semi-permanently attached via screws 44 with an adapter 46, which in turn is recessed into the inner pole shoe 12 and firmly secured via a connection screw 48. The adapter 46 also has bushes 34 to take plug sockets 40, 42.

If screws 44 are undone the transducer head 10 can be removed and exchanged if necessary. This can become the case if the electro-dynamic transducer is required for other materials and/or other workpiece dimensions.

Independently of this, the sliding protection element 22 can itself be removed from the probe head 10 by releasing screws 50 allowing it to be easily inspected, and exchanged if necessary.

We claim:

1. Electro-dynamic transducer for non-destructive testing of workpieces by means of ultra-sonics using a magnet with a magnet yoke with external pole shoe surrounding a conically tapered inner pole shoe, preferably tapering towards the workpiece and equipped in the region of its free face opposite to the workpiece with exciter and receiver coils, which in turn are provided with a cover at least on the side facing the workpiece, characterized in that, the cover encompasses a protective cap (20, 38) spaced from the exciter and receiver coil and covering it, this protective cap in turn is at least partially surrounded by a sliding protection element (22) whereby the said sliding protection element has a basic member (24) with sections (26) which come into contact with the workpiece (14); these sections are introduced into recesses (28) in the basic member by deposit welding, and are formed by metal particles fused into a matrix.

2. According to claim 1, characterized in that, sections (26) formed by deposit welding project at least in parts relative to that face of the basic member (24) turned towards the workpiece (14).

3. According to claim 1, characterized in that, the matrix consists of carbon steel and the metal particles are of hard alloy.

4. According to claim 3, characterized in that, the hardness of the metal particles lies in the range 1.500 VHN to 2.500 VHN, preferably equaling approximately 2.000 VHN.

5. According to claim 1, characterized in that, the basic member (24) is made of austenitic steel.

6. According to claim 1, characterized in that, the protective cap (20) consists of metal preferably with a nitrated surface, and has radially arranged slots.

7. According to claim 6, characterized in that, the protective cap (20) in the shape of a truncated cone has an outwards chamfered lower rim running parallel to the face surface (18), and is in contact with a cap carrier (36) where it is clear of the face of the inner pole shoe (12, 16); in turn the cap carrier must be supportable on the inner pole shoe (16).

8. According to claim 7, characterized in that, the cap carrier (36) consists of a resin bonded fabric such as epoxy-resin material.

9. According to claim 6, characterized in that, the inside surface of the protective cap (20) is coated with a resin bonded fabric at least in the region of the slots.

10. According to claim 9, characterized in that, the resin bonded fabric layer is stuck to the inside surface.

11. According to claim 1, characterized in that, the protective cap is a layer of synthetic stone, such as sapphire.

12. According to claim 11, characterized in that, the inside surface of the layer of synthetic stone facing the coil is provided with a resin bonded fabric coating.

13. According to claim 1, characterized in that, the sliding protection element (22) together with the protective cap (20, 38), the cap carrier (36), the section (16) of the inner pole shoe (12) facing the workpiece (14) and the exciter and receiver coils mounted on it are arranged as a transducer head semi-permanently mounted on the inner pole shoe (12).

14. According to claim 13, characterized in that, the semi-permanent mechanical and/or electrical connection between the transducer head (10) and the lower section of inner pole shoe (12, 46) is made by a plug-and-socket connector.

15. According to claim 13, characterized in that, the sliding protection element (22) is separately removable from the transducer head (10).

* * * * *